(12) United States Patent
Bardoux et al.

(10) Patent No.: US 7,168,322 B2
(45) Date of Patent: Jan. 30, 2007

(54) METHOD FOR ULTRASONIC CONTROL OF WELD JOINTS

(75) Inventors: Olivier Bardoux, Courbevoie (FR); Mario Cence, Saint Vallerin (FR); Sophie Wastiaux, Aulnay s/Bois (FR)

(73) Assignee: L'Air Liquide Société Anonyme à Directoire et Conseil de Surveillance pour l'Etude et l'Exploitation des Procédés Georges Claude, Paris (FR)

( * ) Notice: Subject to any disclaimer, the term of this patent is extended or adjusted under 35 U.S.C. 154(b) by 0 days.

(21) Appl. No.: 10/518,139

(22) PCT Filed: Jun. 13, 2003

(86) PCT No.: PCT/FR03/01798

§ 371 (c)(1),
(2), (4) Date: Dec. 10, 2004

(87) PCT Pub. No.: WO03/106994

PCT Pub. Date: Dec. 24, 2003

(65) Prior Publication Data

US 2005/0223807 A1    Oct. 13, 2005

(30) Foreign Application Priority Data

Jun. 17, 2002   (FR)  .................................. 02 07441

(51) Int. Cl.
*G01N 29/14* (2006.01)

(52) U.S. Cl. .......................... 73/588; 73/597; 73/602; 73/628

(58) Field of Classification Search ................ 73/588, 73/599, 600, 602, 620, 622, 624, 628, 629, 73/632, 597, 598
See application file for complete search history.

(56) References Cited

U.S. PATENT DOCUMENTS

| 3,201,864 | A | * | 8/1965 | Jones et al. ............... 228/110.1 |
| 3,302,453 | A | * | 2/1967 | Wood et al. ................... 73/622 |
| 3,332,278 | A | * | 7/1967 | Wood et al. ................... 73/602 |
| 3,436,958 | A | * | 4/1969 | Proctor ........................ 73/600 |
| 3,540,267 | A | * | 11/1970 | Wood .......................... 73/622 |
| 3,868,847 | A |   | 3/1975 | Gunkel |
| 4,106,326 | A | * | 8/1978 | Lather et al. ................. 73/1.86 |

(Continued)

FOREIGN PATENT DOCUMENTS

EP           0 166 666        1/1986

(Continued)

OTHER PUBLICATIONS

International Search Report for PCT/FR03/01798.

(Continued)

*Primary Examiner*—Hezron Williams
*Assistant Examiner*—Jacques Saint-Surin
(74) *Attorney, Agent, or Firm*—Elwood L. Haynes (57) ABSTRACT

The invention concerns a method for non-destructive ultrasonic control, combining time-of-flight diffraction (TOFD) and inclined longitudinal wave techniques, of weld joints assembling two abutted parts. The method consists of using the time-of-flight diffraction technique, displacing in the longitudinal or circumferential direction, along the weld joint to be controlled, at least one pair consisting of a first transducer and of a second transducer, one transmitting and the other receiving ultrasonic waves, these transducers being laterally positioned on either side of the joint to be controlled, these transducers comprising piezoelectric ceramics or crystals. Furthermore, it consists of displacing along the welded joint to be controlled, using the inclined longitudinal wave technique, at least a third transducer, so as to detect any defect of the joint located at a thickness ranging between 0.5 mm and 15 mm.

25 Claims, 5 Drawing Sheets

U.S. PATENT DOCUMENTS

| | | | |
|---|---|---|---|
| 4,924,707 A | | 5/1990 | Kliesch |
| 5,677,490 A | * | 10/1997 | Gunther et al. ............... 73/622 |
| 5,804,730 A | | 9/1998 | Pfannenstiel et al. |
| 5,814,731 A | * | 9/1998 | Alexander et al. ............ 73/644 |
| 6,125,704 A | * | 10/2000 | Wang .......................... 73/602 |
| 6,138,514 A | * | 10/2000 | Iwamoto et al. ............... 73/622 |
| 6,332,361 B1 | * | 12/2001 | Yamada et al. ............... 73/627 |
| 6,405,596 B1 | * | 6/2002 | Kruzic ........................ 73/611 |
| 6,497,150 B1 | * | 12/2002 | Kruzic ........................ 73/611 |
| 6,535,828 B1 | * | 3/2003 | Furukawa et al. ............ 702/56 |
| 7,093,490 B1 | * | 8/2006 | Kono et al. ................... 73/602 |

FOREIGN PATENT DOCUMENTS

| | | |
|---|---|---|
| EP | 0 305 637 | 3/1989 |
| EP | 0 816 840 | 1/1998 |
| GB | 2 195 022 | 3/1988 |
| GB | 2 198 532 | 6/1988 |
| GB | 2 219 907 | 12/1989 |
| WO | WO 02 31487 | 4/2002 |
| WO | WO 02 44709 | 6/2002 |

OTHER PUBLICATIONS

Lilly J. et al.: *"In-line inspection using time-of-flight diffraction"*, Welding & Metal Fabrication, IPC Ltd., Haywards Heath, GB, vol. 59, No. 8, Oct. 1, 1991, pp. 457-458, 460.

* cited by examiner

METHOD FOR ULTRASONIC CONTROL OF WELD JOINTS

BACKGROUND

The present invention relates to a method for the nondestructive inspection, by ultrasound, of materials and, more particularly, of welds joining two metal workpieces together, edge to edge, in particular of the plate or sheet kind.

This method makes it possible to inspect, during manufacture and in service, structures and equipment comprising welds, for example those obtained by local melting, which joints may contain plane flaws of the crack kind or volume flaws; in this regard, the terms "flaw" and "crack" will be used below without distinction.

As non-limiting examples, the method according to the invention may apply to the inspection of the welds of the walls of equipment or components operating under pressure, forming part of chemical or petrochemical units, nuclear power stations or the like, structures of rotating machines, elements or components of rotating machines, or pipes, in situations that may require inspections, and especially repeated examinations, such as examinations before and after a heat treatment, or before and after a repair, the monitoring, in use, of materials or assemblies, the monitoring of any change in flaws in the pressurized equipment (such as cracks changing in service), industrial quality control in manufacturing, etc.

One particular technique called TOFD (time-of-flight diffraction), applicable to ultrasonic inspection, was developed by M Silk from 1973 onwards and is described, for example, in British Standard BS 7706: 1993 or in the work by J P Charlesworth and JAG Temple *"Engineering Applications of Ultrasonic Time-of-Flight Diffraction"* (1989–2001).

However, no document has indicated, hitherto, means for effective detection, by simple echography, random flaws located in a weld volume at between 5 mm and 100 mm in depth.

This is because the main difficulties presently encountered during an ultrasonic examination using the TOFD technique, which are awaiting industrial solutions, are the following:

in the case for example of a pair of ultrasonic transducers in contact with a non-plane surface of the component to be examined, it is generally necessary to change transducer for complete examination of a joint between walls having thicknesses of between 5 mm and 100 mm;

actual cracks are not always detected with the conventional procedures, mentioning ranges of transducers or of refraction angles that are too blurred;

it is also necessary to change a pair of transducers in order to use different distances between points of emergence and fraction angles adapted to the various thicknesses, such as for example when searching for flaws that may be located near the surface of the weld or, on the contrary, close to the wall on the opposite side from the weld surface; and when searching for flaws of the crack type, no rating criterion exists that can ensure 100% detection of emergent cracks or of internal cracks likely to emerge on the internal or external surface, and the correlation of which, with a radiographic examination, has demonstrated better performance than the ultrasonic technique.

To try to solve these problems, a number of solutions have already been proposed.

Thus, document GB-A-2 198 532 has proposed an inspection method of the TOFD (time-of-flight diffraction) type for welded objects under water, such as oil extraction platforms, using two transducers adjacent the surface of the object to be inspected and spaced apart, one on either side of the weld joint, in which any cracks have to be detected.

However, the solutions proposed up until now have proved unsatisfactory, insufficient or imperfect from the industrial standpoint, especially as they do not allow effective detection of cracks in the welds.

The present invention aims to solve the problems existing in the prior art by proposing an improved method of inspecting welds that effectively covers at least the depth range between 5 mm and at least 60 mm, in a single pass along the weld to be inspected, whether along the longitudinal direction or the circumferential direction, i.e. for linear welds or circular welds (butt welding of tubes), and also the smaller depth range, namely the regions close to the surface at a depth of between 0.5 mm and 5 mm, which are usually more difficult to inspect.

In addition, the invention also aims to allow auscultation of a larger thickness or volume region using a reasonable number of transducers.

Finally, the object of this invention is also to provide a simple and autonomous apparatus suitable for implementing the inspection method in question from an industrial standpoint.

The solution of the present invention is therefore a method for ultrasonic inspection of welds that combines the TOFD technique with the CW (creeping wave) technique.

SUMMARY

More precisely, the invention relates to a method for ultrasonic inspection of welds, more particularly welds joining two metal workpieces edge to edge, in which, to inspect the joint:

a) applying the TOFD technique, at least one pair of transducers, formed from a first transducer and a second transducer, one emitting ultrasonic waves and the other receiving ultrasonic waves, is moved in the longitudinal or circumferential direction along the weld to be inspected, said transducers being positioned laterally on either side of the joint to be inspected and said transducers comprising piezoelectric crystals or ceramics, so as to detect any flaw in the joint located at a depth of at least 5 mm and preferably up to 60 mm; and b) applying the inclined-longitudinal wave or creeping wave (CW) technique, at least one third transducer is moved along the weld to be inspected so as to detect any flaw in the joint located at a depth of between 0.5 and 15 mm.

BRIEF DESCRIPTION OF THE DRAWINGS

For a further understanding of the nature and objects for the present invention, reference should be made to the following detailed description, taken in conjunction with the accompanying drawings, in which like elements are given the same or analogous reference numbers and wherein.

DESCRIPTION OF PREFERRED EMBODIMENTS

Depending on the case, the method of the invention may include one or more of the following technical features:

- at step a), the first and second transducers comprise piezoelectric crystals or ceramics of rectangular or oblong shape;
- in step a), the ultrasonic transducers have a frequency band greater than 60% of the central frequency and a frequency between 1 and 20 MHz, preferably between 6 and 18 MHz.
- it includes the lateral shift (D) of the pair of ultrasonic transducers relative to the center or axis of the weld.
- in step a), any flaw in the joint located at a depth of at least 10 mm, preferably between 10 and 300 mm and even more preferably 10 to 60 mm is detected.
- in step b), the CW technique is implemented by injecting sound into at least part of the joint to be inspected with longitudinal sound waves inclined at an angle ($\beta$) of between 70 and 90°, preferably about 76° of angle of refraction, and/or at a frequency of between 1.5 and 4 MHz, in particular around 2 MHz.
- step b) is carried out in succession on each side of the weld to be inspected.
- in step b), any flaw in the joint located at a Method for ultrasonic inspection of welds depth of between 0.5 mm and 20 mm, preferably 0.5 mm to 10 mm, is detected.
- in step b), at least one third transducer is used, said transducer comprising a wave-emitting ceramic allowing sound waves to be emitted in the direction of the weld and an ultrasonic wave receiving ceramic for receiving ultrasonic waves.
- it includes a calibration phase in which the pair or pairs of ultrasonic transducers are calibrated on the basis of a calibration notch of defined depth, simulating a crack, preferably a notch with a length of about 10 mm at a depth of around 1 mm.
- it includes at least one analysis step in which at least one signal received by the or each receiving transducer is analyzed, while the weld is being scanned, so as to detect any flaw, especially any crack, and preferably to determine or evaluate the depth or length thereof; and
- the thickness (e) is between 5 mm and at least 60 mm, and the workpieces are walls of equipment or components operating under pressure, forming part of chemical or petrochemical units, nuclear power stations or the like, structures of flying machines, elements or components of rotating machines, pipes, railroad rails or any other all-welded assembly.

Preferably, the method uses ultrasonic transducers of this kind with a broad frequency band, in particular greater than 60% of the central frequency, and having very short pulses, that is to say high frequencies, especially between 1 and 20 MHz and preferably between 6 and 18 MHz.

The method according to the invention also comprises, advantageously, the adaptation of the separation between the two ultrasonic transducers, one the transmitter and the other the receiver, and/or the lateral shifting of this pair of transducers relative to the center of the weld to be inspected, in order to cover, optimally, with this single pair of transducers, a volume corresponding to the thickness of the weld to be inspected, and possibly including zones adjacent this weld. In particular, the setting of the separation between the two points of emergence can be adapted here in order for the reflection echo from the opposite wall being inspected to have its amplitude close to the maximum.

It is clear that with more numerous pairs of transducers, the method may also allow, in a single pass, the auscultation of greater thicknesses, possibly up to 300 mm.

It should be noted that the processing procedure here takes into account not only the information contained in the usual signals, ranging from the lateral wave to the bottom echo, but also the information generated by secondary waves, such as mode transformations.

Specifically, this is made possible by the claimed use of broad-band (greater than 60% of the central frequency) transducers operating at high frequencies, preferably between 6 and 18 MHz.

The method forming the subject of the invention thus allows detection, rapidly, that is to say detection of any type of flaw over the entire weld, the depth of the cracks being able to be measured with a precision of ±0.25 mm.

To achieve such precision, it is advantageous to carry out beforehand a calibration phase in which the pair or pairs of ultrasonic transducers used for carrying out the TOFD method are calibrated on the basis of a calibration notch, in particular an electro-eroded notch, of defined depth, located on one face of a calibration block, such an artificial notch simulating a crack. This notch may especially have a thickness of between 0.5 mm and half the thickness of a calibration block, the thickness of which corresponds to that of the workpieces bearing the weld to be examined, or even on one of the workpieces themselves; in this case, the notch may be made on a face on the opposite side from its weld surface. In particular, the notch may have a width of about 1 mm when it is desired to detect very narrow cracks.

The apparatus according to the invention for implementing this method comprises:

- at least one pair of transducers formed from first and second transducers, one emitting ultrasonic waves and the other receiving them, said transducers using piezoelectric crystals or ceramics and the two transducers being mechanically linked via a common support that holds them in place at a certain distance (E) apart, and also being connected to a liquid, in particular water, inlet for acoustic coupling of these transducers with the element to be inspected;

at least one third transducer; and processing means for processing the measurements, the transducers still being connected to said measurement processing means.

Depending on the case, the apparatus of the invention may include one or more of the following technical features:

the common support for the two transducers, one an ultrasonic wave transmitter and the other an ultrasonic wave receiver, comprises a rod linkage system designed to allow the gap (E) between these two ultrasonic transducers to be adjusted;

the rod linkage system for supporting the two ultrasonic transducers also includes a pivoting arrangement for pivoting each transducer, with locking means for locking them in a chosen angular position;

the common support for the two ultrasonic transducers possesses an arrangement allowing the pair of transducers to undergo a lateral shift (D) relative to the center of the weld to be inspected;

said third transducer comprises a wave emitting ceramic, allowing sound waves to be emitted, and a sound wave receiving ceramic, allowing sound waves to be received; and the common support for the two TOFD transducers, one the transmitter and the other the receiver of the ultrasonic waves, comprises a rod linkage system designed to allow the separation between these two ultrasonic transducers to be adjusted. Advantageously, the rod linkage system for supporting the two ultrasonic transducers also includes a pivoting arrangement for each transducer, with locking means, for locking in a chosen angular position, which makes it possible to adjust the contact of the transducers on a surface of imperfect flatness or to adapt their inclination depending on the radius of curvature of the element to be inspected, if the latter has a curved, for example cylindrical, surface. To optimize the scanning of the weld to be inspected, the common support for the two ultrasonic transducers may furthermore have an arrangement for shifting the pair of transducers laterally relative to the center of the weld to be inspected.

As regards the means for processing the measurements, these may be performed using techniques known in the field of ultrasonic measurement and inspection equipment. In particular, the measurements taken may be stored in memory, to be processed subsequently by a software package or by specific calculations, with the aim of forming and displaying what are called "A-scan" and/or "B-scan" images, and to extract from these images the anomalies or other discriminatory signs of flaws in the welds inspected, so as to result in a visual interpretation, in real time or subsequently, by analysis of the signal in automatic mode.

A library of standard images may in this case help the operators to take decisions about any further examination to be carried out, and/or to make a diagnostic regarding the nature of the flaws revealed. Here, a specific software package may also provide complementary means to ascertain the type of flaw detected, and in particular the volumetric nature or otherwise of the flaw analyzed.

Moreover, an analytical method of the "cascade" type, recommended by the standards, may also be used.

Figure 1:
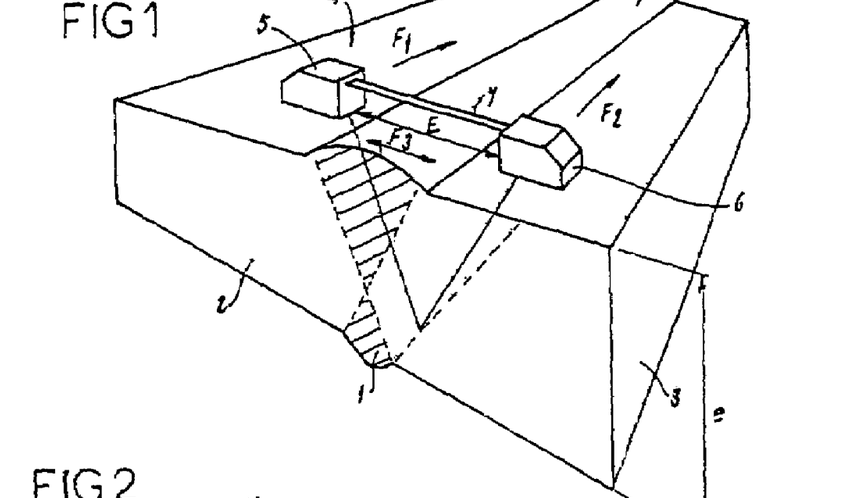
FIG. 1 illustrates a stylized view showing the principle of the sonification step using the TOFD technique in accordance with one illustrative embodiment of the present invention.

As illustrated in FIG. 1, the invention relates to the TOFD inspection of a weld 1, which joins two metal workpieces 2, 3 together, edge to edge, such as plates, in particular those with beveled edges, the assembly having a given thickness e, typically between 5 mm and 100 mm.

The apparatus for implementing the method so as to inspect the weld 1 and the adjacent zones, in particular for detecting any flaws of the crack kind, is brought up to and moved along the weld to be inspected, that is to say moved over one face of the assembly formed by the weld 1 and the two workpieces 2, 3 welded together.

This apparatus comprises, as the general "acquisition" part 4, essentially two transducers 5, 6, one an ultrasonic wave transmitter and the other an ultrasonic wave receiver, being connected together by a rod linkage system 7 that keeps them apart with a separation E.

The two transducers 5, 6 are placed on top of the edges of the two respective workpieces 2, 3, on either side of the weld 1, the rod linkage system 7 straddling this weld 1 so as to lie transversely to it.

These transistors 5 and 6 are moved along the weld by scanning, along the direction of the arrows F1 and F2, parallel to the longitudinal direction of the weld 1, a single scan being sufficient here to auscultate the entire weld 1.

Preferably, as indicated by the double arrow F3, provision is also made to modify the separation E between the two transducers 5, 6 and/or to shift these two transducers 5, 6 laterally in order to adapt the apparatus to the particular features of each weld 1 and thus increase the possible applications of this apparatus.

Figure 2:
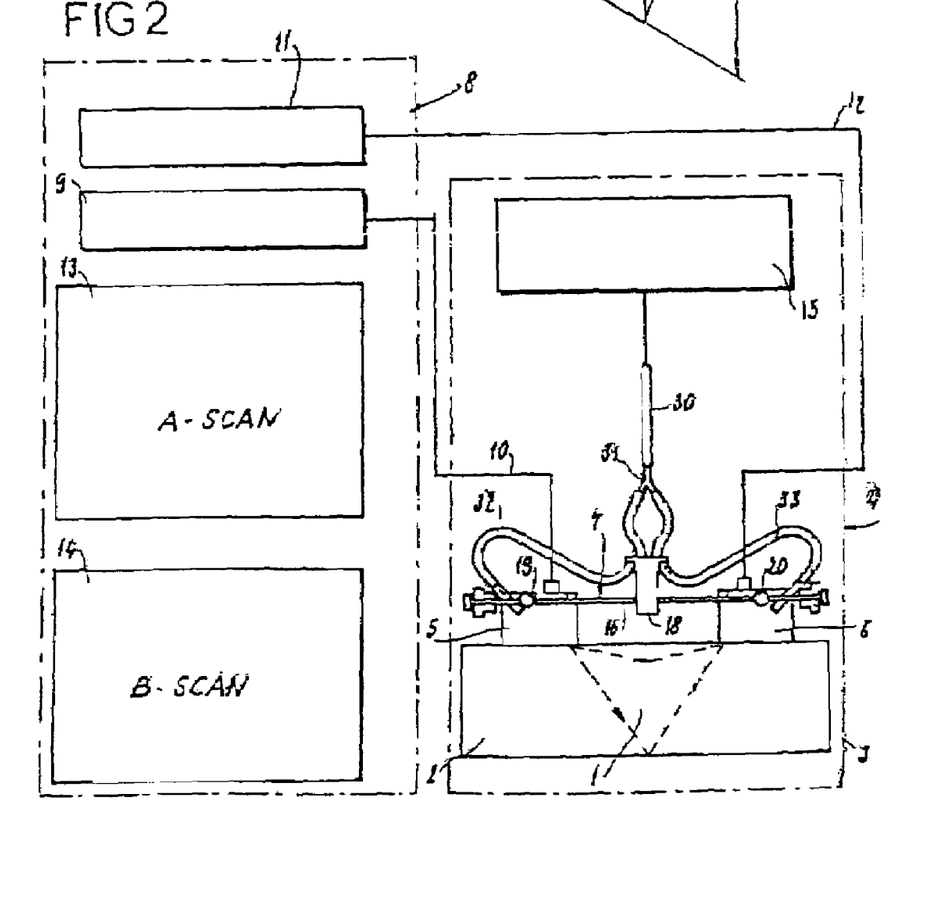
FIG. 2 illustrates a block diagram of the apparatus in accordance with one illustrative embodiment of the present invention.

FIG. 2 is a block diagram of the apparatus showing, on the right, its "acquisition" part 4 with the two transducers 5, 6 connected by the rod linkage system 7 and, on the left, the electronic part 8, which is connected to the "acquisition" part 4 and in particular processes and displays the measurements taken.

The electronic part 8 comprises an ultrasonic transmitter 9, connected at 10 to the ultrasonic wave transmitter transducer 5, and an ultrasonic receiver 11, connected at 12 to the ultrasonic wave receiver transducer 6.

Display means 13, 14, for displaying A-scan and B-scan images respectively, are provided in the electronic part 8.

The acquisition part 4 furthermore includes an autonomous pressurized-water feed system, shown schematically at 15, which is connected to the two transducers 5, 6 via hoses (explained in detail below).

Figure 3:
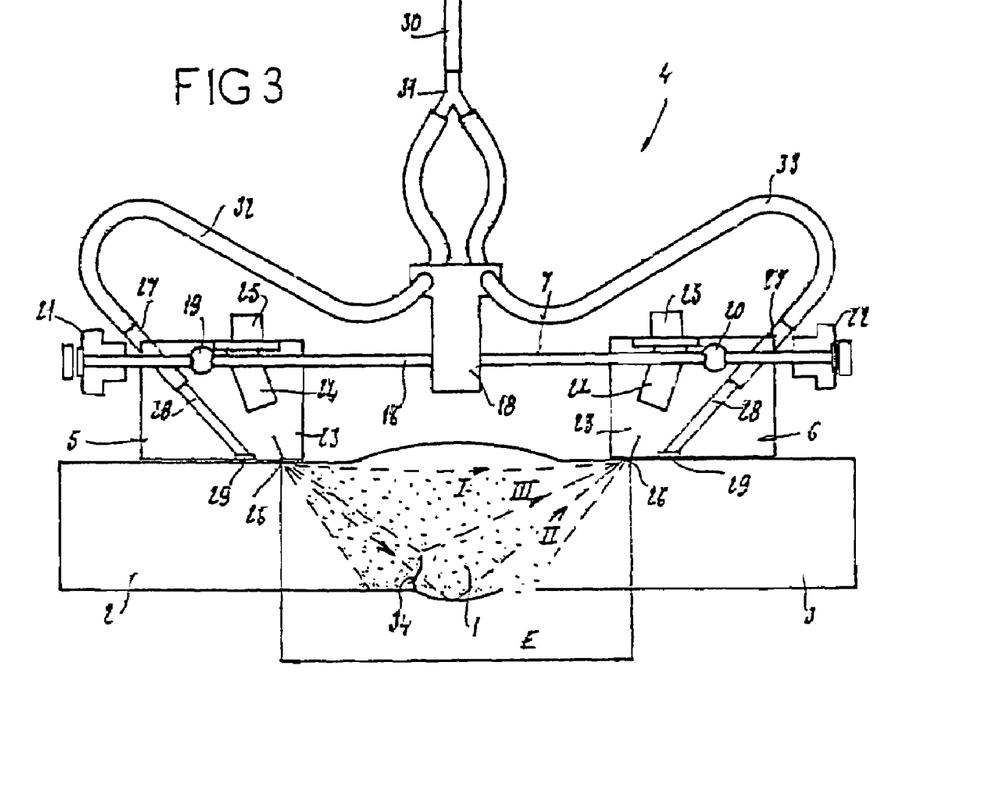
FIG. 3 illustrates a front view of the 'acquisition' part of this apparatus in accordance with one illustrative embodiment of the present invention.
Figure 4:
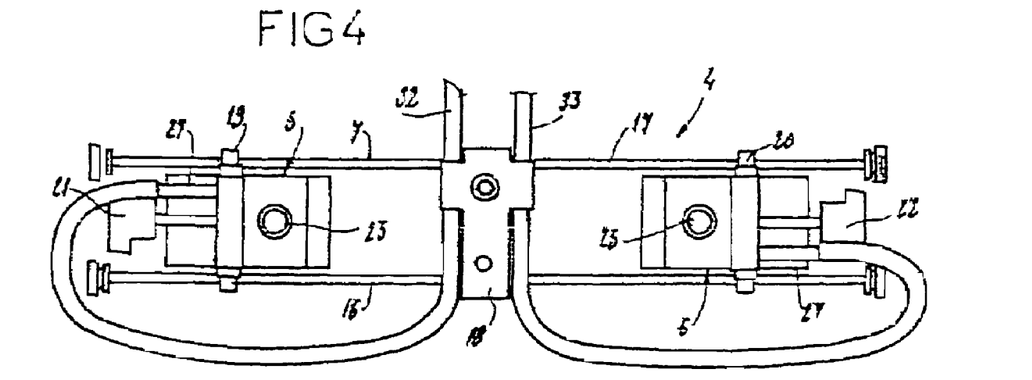
FIG. 4 illustrates a plan view from above, corresponding to FIG. 3.

FIG. 3 et seq. show in greater detail the structure of the acquisition part 4.

The rod linkage system 7 is composed of two parallel straight rods 16 and 17 held by a common central support 18. Two transverse spindles 19 and 20 are mounted so as to slide on these rods 16 and 17, on either side of the central support 18. The first transverse spindle 19 serves for supporting the transducer 5 and the second transverse spindle 20 serves for supporting the other transducer 6, the arrangement being symmetrical.

Each transducer 5 and 6 is thus mounted so as to move in linear displacement along the rods 16 and 17 of the rod linkage system 7, thereby making it possible to adjust the separation E between the two transducers 5 and 6.

In addition, the inclination of the two transducers 5, 6 can be adjusted, by pivoting about the respective spindles 19 and 20. Respective lock screws 21 and 22 are provided for immobilizing the two transducers 5 and 6 in the chosen angular positions.

In detail, each transducer 5 or 6 comprises:

a body 23, which is provided with a tapped hole for accommodating the lock screw 21 or 22, through which body the spindle 19 or 20 passes;

a block 24, inserted into the body 23 and combining a piezoelectric element and its damper;

on the upper face of the body 23, a connector 25 for the piezoelectric element 24 (connecting it to the link 10 or 12);

on the lower face of the body 23, a point of emergence 26 of the ultrasonic beam; and a water inlet fitting 27 connected, via a channel 28 internal to the body 23, to a water outlet 29 located on the lower face of said body 23.

The pressurized-water feed system 15 also includes a common pipe 30 terminating in a delivery "Y" 31, from which two hoses 32, 33 leave, these terminating respectively in the two transducers 5, 6, more particularly in the water inlet fitting 27 of each transducer. Thus, the acoustic coupling between each transducer 5 or 6 and the element to be inspected, on which this transducer is applied, is produced by means of a layer of water.

The piezoelectric elements 24 of the two transducers 5 and 6 are rectangular or oblong piezoelectric ceramics, for example with dimensions of 6×4 mm, operating in longitudinal wave mode, it being possible for the acoustic beam to be at an angle ranging from 30° to 80°, preferably from 50° to 70°.

The operating frequencies are between 1 and 20 MHz, preferably between 6 and 18 MHz and even more preferably between 6.5 MHz and 8.5 MHz, for thicknesses of less than 10 mm, or between 15 and 20 MHz, preferably around 18 MHz, for thicknesses of less than 10 mm, and/or with an associated −6 dB bandwidth of 75% ±25% relative to the central frequency.

In fact, rectangular ceramics with a length of between 5 and 20 mm and a width of between 2 and 8 mm can be used.

By using oblong or rectangular ceramics it is possible to achieve a high divergence of the ultrasonic beam and therefore complete sonification of the volume to be inspected.

For example, TOFD transducers with the reference 5-60 OL 55, sold by Metalscan may be used.

As an example, a 30 to 65° acoustic beam can be used to inspect thickness ranges between 10 and 300 mm. A refraction angle in steel of around 53 to 58°, preferably about 55°, is thus recommended for a weld thickness of between 5 and 60 mm.

In use, as illustrated in FIG. 3, the separation E of the two transducers 5, 6, more particularly of their respective points of emergence 26, is adjusted according to the width and the thickness of the weld 1.

FIG. 3 indicates, at I, the ultrasonic path of the lateral wave and, at II, the path of the bottom echo, the "sonified" volume being indicated by the shading.

If a crack 34 is present in this volume, the tip of the crack 34 behaves like a secondary source of spherical waves (diffracted waves).

FIG. 3 also indicates, at III, the ultrasonic path of the diffraction echo at the tip of the crack 34.

By analyzing the signal received by the receiver transducer 6, during the scan of the weld 1, it is possible to detect such a crack 34 and to measure its depth.

In receive mode, a battery-operated 24 dB preamplifier may be used to improve the "signal to noise" ratio.

The representation of the signals received may in particular be displayed, at 14, in "rectified B-scan" mode, that is to say with a display of the time as a function of the signal amplitude.

Figure 5:
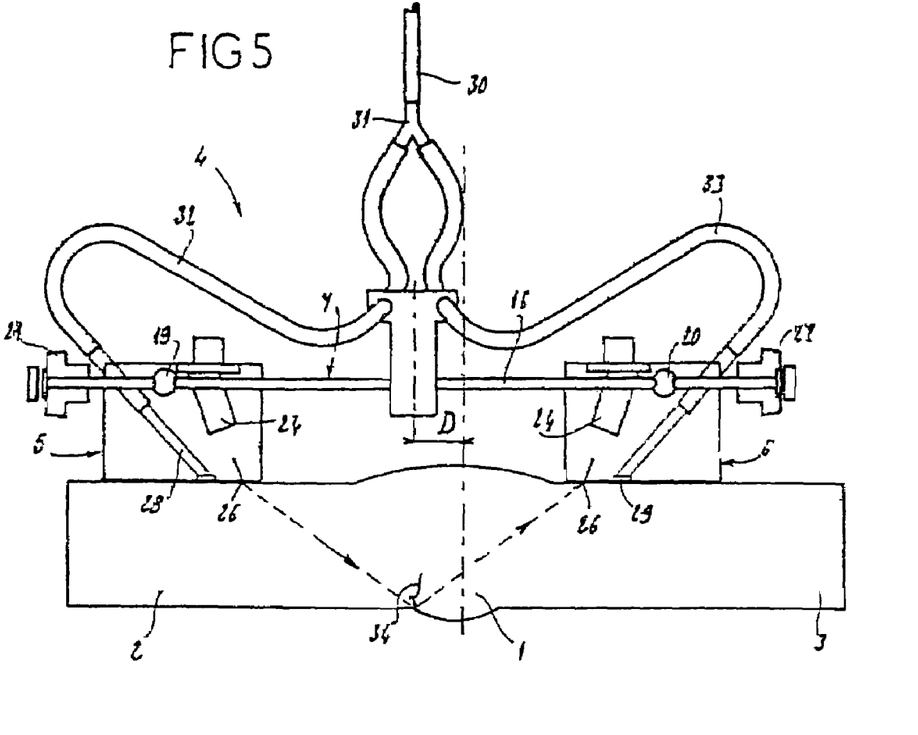
FIG. 5 illustrates an alternate implementation similar to FIG. 3, illustrating the lateral shift of the transducers used for implementing the TOFD technique.

As illustrated in FIG. 5, a lateral shift D of the combination of the two transducers 5, 6, on one side or the other of the center of the weld 1, can help in the search for flaws at the border of this weld 1.

Figure 6:
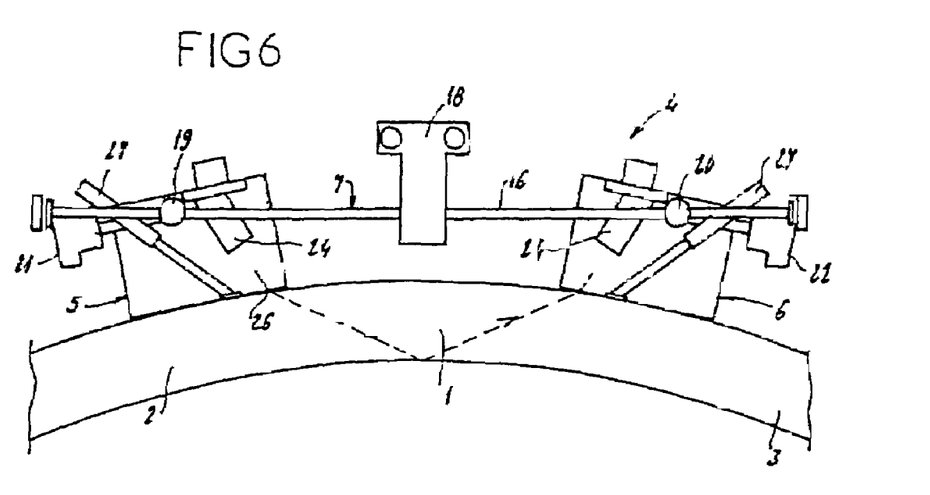
FIG. 6 illustrates an alternate implementation similar to FIG. 3, illustrating the adaptation of an element to be inspected, which has a radius of curvature.

Finally, as illustrated in FIG. 6, by adjusting the inclination of the two transducers 5, 6 it is possible to adapt the apparatus to an element to be inspected that has a relatively large radius of curvature.

According to the invention, it is very important to provide a calibration phase in which the or each pair of ultrasonic transducers 5, 6 is calibrated on the basis of an electro-eroded notch of defined depth, which simulates a crack.

This is because, without such a prior calibration step, effective detection of cracks in the weld may be compromised.

According to the invention, detection using the TOFD technique described above is combined with detection using the CW technique.

Such a TOFD/CW combination has in fact proved to be particularly advantageous as it allows effective detection of cracks with an apparatus consisting of three inspection channels, that is to say with three transducers, and to do so not only for flaws such as cracks at more than 5 mm in depth, but also those at less than 5 mm in depth, which are sometimes masked by the lateral wave during examination using just the TOFD technique.

To do this, at least three transducers are used so as to completely cover the entire "sonified" volume.

However, it is possible to use more than three transducers so as to refine and/or further improve the detection, for example TOFD transducers at different angles or shear-wave transducers.

As previously, the signals are then analyzed by A-scan, B-scan, C-scan and/or D-scan imaging by means of a filtering system, in real time or subsequently, or using a calculation system capable of characterizing the indication detected. Preferably, the VENUS software from Metalscan is used, this software generating signal representations in B-scan or D-scan mode using a high-frequency (HF) signal, or else the MIDAS software from Tecnatom, or any other equivalent software.

The frequency components of the recorded signals may also be measured by Fourier transform analysis.

In fact, the CW technique allows surface flaws, whether emerging or not emerging at the surface, to be detected down to depths ranging from 0.5 mm to about 18 mm, depending on the case, thereby allowing effective supplementary examination of the thickness region proving to be never optimal using the TOFD technique.

Such a combination of the TOFD and CW techniques has never been described hitherto and is particularly advantageous from the industrial standpoint, the more so when the examination is preceded by a calibration phase, since this TOFD/CW combination makes it possible to detect volume or non-volume flaws in welds over practically their entire thickness, that is to say over the sonified volume, whether these be near the surface (0.5 mm to 18 mm) or deeper in the weld (beyond 18 mm and up to 300 mm in depth).

In practice, the minimum size of discontinuities and other cracks that can be effectively detected by the TOFD and CW techniques is around 0.5 mm, whereas the maximum size corresponds to a through-crack, that is to say one right through the thickness of the weld.

Preferably, the CW technique is used for inspecting cracks of less than 5 mm that are located on the same side as the probe face, by sonification with creeping waves with a refraction angle of between 70 and 90°, preferably about 76°, and with a frequency between 1.5 and 4 MHz, for example around 2 MHz.

The ceramic(s) used to implement the CW technique are preferably rectangular, for example with dimensions of 5×10 mm, both ceramics forming a transducer that operates in separate transmit and receive mode, and/or for a roof angle between 5 and 15°, preferably around 10°.

Standard transducers of the FIDM 76-2 type sold by Metalscan may be used.

Figure 7:
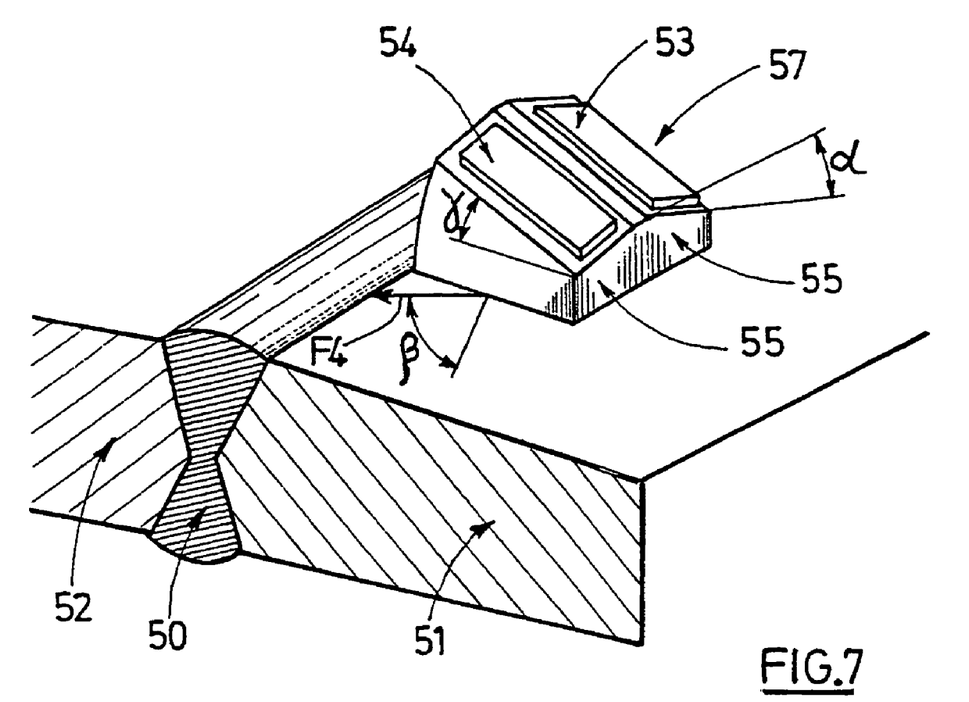
FIG. 7 illustrates the principle of implementation of the creeping wave technique in accordance with one illustrative embodiment of the present invention.

FIG. 7 shows schematically a transducer 57 that can be used for implementing the CW technique so as to transmit creeping waves (arrow F4) for detecting shallow flaws in a weld 50 joining two metal workpieces 51, 52 together.

The transducer 57 is composed of a longitudinal-wave transmit ceramic 53 and a sound-wave receive ceramic 54 both supported by an inclined shoe 55, for example made of PMMA, such as Plexiglas, or the like, which makes an angle of about 27° (±2°) with the surface of the workpiece in the plane of incidence.

The roof angle $\alpha$ of the ceramics 53, 54 is between 5 and 15°, preferably around 10°.

The refracted longitudinal sound waves are sent along the direction of the arrow F4 toward the weld 50 at an angle $\beta$ of around 76° to the surface of the workpiece.

The angle $\gamma$ is between 26 and 29° and corresponds to the angle of incidence of the shoe machined in PMMA.

Figure 8:
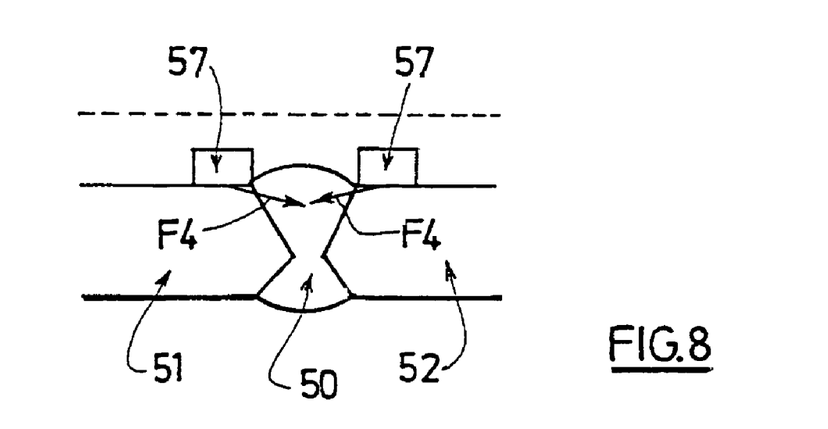
FIG. 8 illustrates an alternate implementation of the principle of the creeping wave technique in accordance with one illustrative embodiment of the present invention.

As shown in FIG. 8, the transducer 57 is passed in succession on either side of the weld 50 and the longitudinal sound waves are sent at the angle $\beta$ of 76° and at a frequency of 2 MHz, thereby allowing complete sonification of the upper volume of the weld 50.

Figure 9:
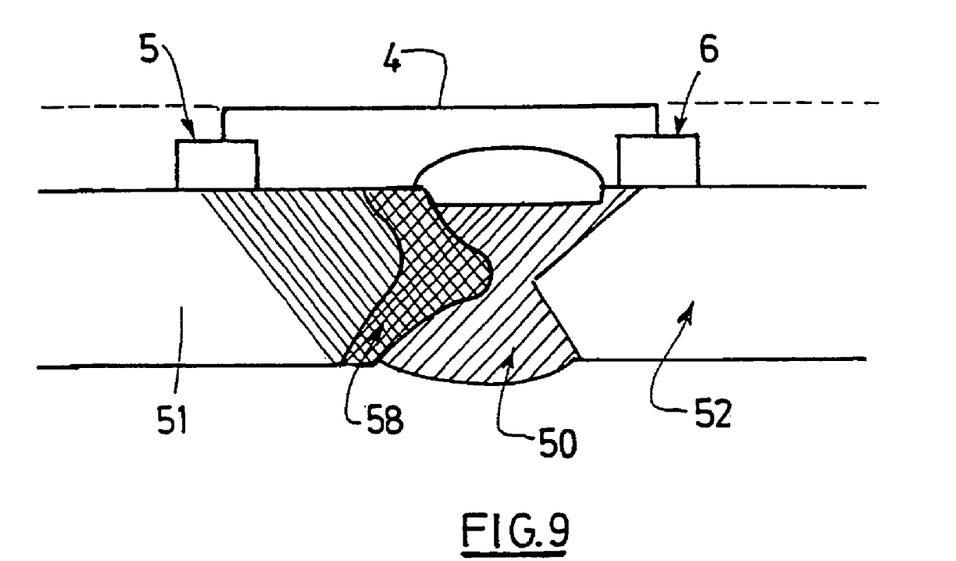
FIG. 9 illustrates a diagram of TOFD detection on a wide weld in accordance with one illustrative embodiment of the present invention.

When the weld 50 has two large a width, the inspection may be supplemented by offset passes in TOFD mode, as shown schematically in FIG. 9 by means of the device comprising the transducers 5, 6 of figure 1, thereby making it possible to cover the entire width to be inspected, that is to say the entire heat-affected zone 58 of the welding.

Figure 10:
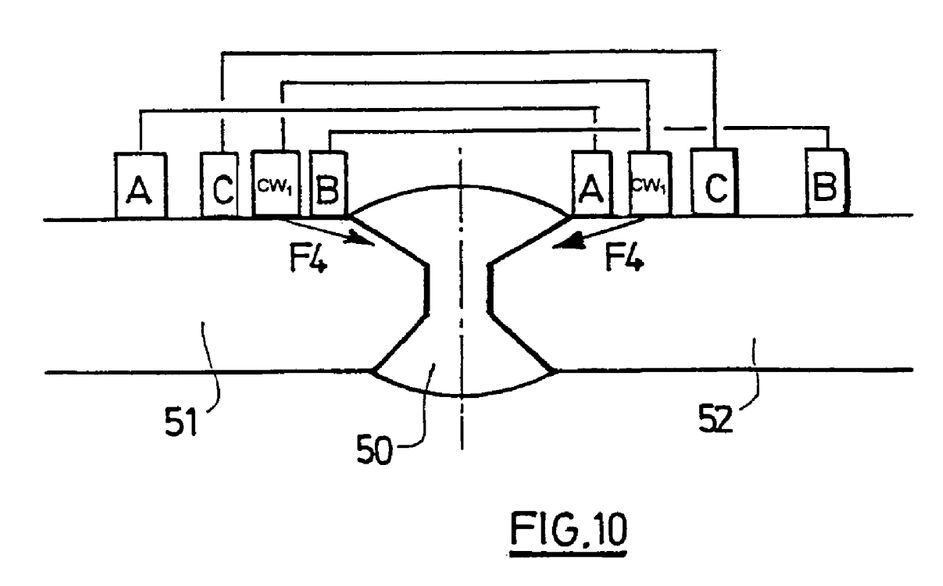
FIG. 10 illustrates diagrammatically the principle of combining TOFD detection with creeping wire detection in accordance with one illustrative embodiment of the present invention.

FIG. 10 shows the principle of how TOFD detection and CW detection are combined according to the invention for a weld 50 between two workpieces 51 and 52.

More precisely, in order for the weld 50 to be inspected very effectively, the method is employed in five passes or scans, namely:

i) centered axial pass along the weld 50, in TOFD mode, with transducers C—C;
ii) passes successively offset to the left and then to the right of the axis of the weld 50 (or vice versa) in TOFD mode, using transducers A—A and B—B;
iii) pass to the left of the weld 50, in CW mode, using transducer $CW_1$; and
iv) pass on the right of the weld, in CW mode, with transducer $CW_2$.

Passes i) and ii) in TOFD mode are made using transducers A—A, B—B and C—C, which here are identical, the waves being sent at an angle of 55° and at a frequency of 7.5 MHz.

Passes iii) and iv) in CW mode are made using transducers $CW_1$ and $CW_2$, which are also identical, the waves then being sent at an angle of 76° and at a frequency of 2 MHz (see arrow F4).

Such a sequence allows very effective detection of cracks, both in terms of length and depth.

However, it would be possible to carry out fewer passes, for example a single axial pass in TOFD mode (pass i)) and one or two passes in CW mode.

Of course, the invention encompasses all alternative embodiments and applications covered by the above principle, in particular whatever the constructional details of the apparatus used, for example the structure of its rod linkage system, the shape of the transducers or their size. For example, electronic focusing using multi-element transducers would also fall within the scope of the invention.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A method for ultrasonic inspection of welds, comprising:
   a) applying the TOFD technique,
      1. said TOFD technique comprising utilizing at least one pair of transducers;
      2. said at least one pair of transducers comprising a first transducer and a second transducer;
      3. said first transducer one emitting ultrasonic waves and said second transducer receiving ultrasonic waves;
      4. said at least one pair of transducers moving in a direction selected from the group consisting of a longitudinal direction along the weld to be inspected and or a circumferential direction along the weld to be inspected;
      5. said at least one pair of transducers being positioned laterally on either side of the weld to be inspected; and
      6. said at least one pair of transducers comprising piezoelectric crystals or ceramics, so as to detect any flaw in the weld located at a first depth of at least about 5 mm; and
   b) applying a creeping wave technique, wherein said creeping wave technique comprises:
      1. moving at least one third transducer along the weld to be inspected so as to detect any flaw in said weld located at a second depth of between about 0.5 mm and about 15 mm; and
      2. injecting sound into at least part of the weld to be inspected with at least one longitudinal sound wave from said third transducer inclined at an angle ($\beta$) of between about 70° and 90° of an angle of refraction, or at a frequency of between about 1.5 MHz and about 4 MHz.

2. The method of claim 1, wherein said welds further comprises joining two metal workpieces edge to edge.

3. The method of claim 2, wherein:
   a) said workpieces comprise a thickness, wherein said thickness is between about 5 mm and about at least 60 mm; and
   b) said workpieces being selected from the group consisting of:
      1) walls of equipment;
      2) components operating under pressure;
      3) part of a chemical unit;
      4) part of a petrochemical unit;
      5) part of a nuclear power station;
      6) structures of flying machines;
      7) elements of rotating machines;
      8) components of rotating machines;
      9) pipes;
      10) railroad rails; and
      11) any all-welded assembly.

4. The method of claim 1, wherein said first transducer and said second transducer are selected from the group consisting of:

a) piezoelectric crystals;
b) ceramics of rectangular shape; and
c) ceramics of oblong shape.

5. The method of claim 1, wherein said ultrasonic transducers have a frequency band greater than about 60% of the central frequency and a frequency between about 1 MHz and about 20 MHz.

6. The method of claim 1, wherein said ultrasonic transducers have a frequency band greater than 60% of the central frequency and a frequency between about 6 MHz and about 18 MHz.

7. The method of claim 1, further comprising the lateral shift of said pair of ultrasonic transducers relative to the center of the weld.

8. The method of claim 1, wherein said first depth is about 10 mm.

9. The method of claim 1, wherein said first depth is between about 10 mm and 300 mm.

10. The method of claim 1, wherein said first depth is between about 10 mm to 60 mm.

11. The method of claim 1, wherein said frequency is about 2 MHz.

12. The method of claim 1, wherein said creeping wire technique comprises injecting sound into at least part of the weld to be inspected with at least one longitudinal sound wave from said third transducer inclined at an angle ($\beta$) of about 76° of angle of refraction, or at a frequency of between about 1.5 MHz and about 4 MHz.

13. The method of claim 12, wherein said frequency is about 2 MHz.

14. The method of claim 1, wherein step b) is carried out in succession on each side of the weld to be inspected.

15. The method of claim 1, wherein, in step b), any flaw in the weld located at a depth of between about 0.5 mm and about 20 mm is detected.

16. The method of claim 1, wherein, in step b), any flaw in the weld located at a depth of between about 0.5 mm and about 10 mm is detected.

17. The method of claim 1, wherein said at least one third transducer comprises a wave-emitting ceramic allowing sound waves to be emitted in the direction of the weld and an ultrasonic wave receiving ceramic for receiving ultrasonic waves.

18. The method of claim 1, further comprising a calibration phase in which said ultrasonic transducers are calibrated on the basis of a calibration notch of defined depth, said notch simulating a crack.

19. The method of claim 18, wherein said calibration notch has a length of about 10 mm and a depth of about 1 mm.

20. The method of claim 1, further comprising at least one analysis step in which at least one signal received by at least one receiving transducer is analyzed, said analysis being performed while the weld is being scanned, said analysis resulting in a result selected from the group consisting of:
   a) the detection of any flaw;
   b) the detection of any crack
   c) the determination of the flaw depth;
   d) the determination of the flaw length
   e) the evaluation of the flaw depth; and
   f) the evaluation of the flaw length.

21. An apparatus for implementing the method of inspection of welds of claim 1, comprising:
   a) at least one pair of transducers,
      1) said at least one pair of transducers comprising a first and a second transducer;
      2) said first transducer emitting ultrasonic waves;
      3) said second transducer receiving ultrasonic waves;
      4) said at least one pair of transducers generating a measurement signal;
      5) said at least one pair of transducers using at least one of piezoelectric crystals or ceramics;
      6) said at least one pair of transducers being mechanically linked via a common support, wherein said common support comprises a rod linkage system which is designed to hold the transducers apart a certain distance and to allow this distance to be adjusted as desired; and
      7) common support being connected to a liquid inlet for acoustic coupling of these transducers with the weld to be inspected;
   b) at least one third transducer; and
   c) processing means for processing said measurement signal, said transducers being connected to said measurement processing means.

22. The apparatus of claim 21, wherein said liquid comprises water.

23. The apparatus of claim 21, wherein said rod linkage further comprises a pivoting arrangement for pivoting each transducer, said rod linkage further comprising a locking means for locking in a chosen angular position.

24. The apparatus of claim 21, wherein said common support further comprises an arrangement allowing said pair of transducers to undergo a lateral shift relative to the center of the weld to be inspected.

25. The apparatus of claim 21, wherein said third transducer further comprises:
   a) a wave emitting ceramic; and
   b) a sound wave receiving ceramic.

* * * * *